US006632237B2

(12) United States Patent
Ben-David et al.

(10) Patent No.: US 6,632,237 B2
(45) Date of Patent: Oct. 14, 2003

(54) DEVICE AND METHOD FOR SEALING A PUNCTURE IN A BLOOD VESSEL

(75) Inventors: Shlomo Ben-David, Tel-Aviv (IL); Yohanan Mageni, Lower Galilee (IL)

(73) Assignee: Bio-Seal Tech, Inc., Garfield, NJ (US)

( * ) Notice: Subject to any disclaimer, the term of this patent is extended or adjusted under 35 U.S.C. 154(b) by 250 days.

(21) Appl. No.: 09/757,623

(22) Filed: Jan. 11, 2001

(65) Prior Publication Data

US 2002/0091410 A1 Jul. 11, 2002

(51) Int. Cl.[7] ............................................... A61B 17/08
(52) U.S. Cl. ........................................................ 606/213
(58) Field of Search ...................... 606/213; 604/167.01

(56) References Cited

U.S. PATENT DOCUMENTS

| 4,705,040 A | | 11/1987 | Mueller et al. | |
|---|---|---|---|---|
| 4,890,612 A | | 1/1990 | Kensey | |
| 4,929,246 A | | 5/1990 | Sinofsky | |
| 5,108,420 A | | 4/1992 | Marks | |
| 5,254,133 A | * | 10/1993 | Seid | 606/215 |
| 5,330,501 A | | 7/1994 | Tovey et al. | 606/198 |
| 5,342,393 A | | 8/1994 | Stack | |
| 5,350,399 A | | 9/1994 | Erlebacher et al. | |
| 5,391,183 A | | 2/1995 | Janzen et al. | |
| 5,492,304 A | * | 2/1996 | Smith et al. | 251/149.1 |
| 5,512,053 A | | 4/1996 | Pearson et al. | 604/167 |
| 5,540,715 A | * | 7/1996 | Katsaros et al. | 606/213 |
| 5,613,974 A | | 3/1997 | Andreas et al. | |
| 5,634,937 A | * | 6/1997 | Mollenauer et al. | 606/213 |
| 5,810,884 A | | 9/1998 | Kim | |
| 5,861,003 A | | 1/1999 | Latson et al. | |
| 5,893,856 A | * | 4/1999 | Jacob et al. | 606/151 |
| 5,957,952 A | | 9/1999 | Gershony et al. | |
| 5,964,782 A | | 10/1999 | Lafontaine et al. | 606/213 |
| 5,984,950 A | | 11/1999 | Cragg et al. | 606/216 |
| 6,007,563 A | | 12/1999 | Nash et al. | |
| 6,197,042 B1 | | 3/2001 | Ginn et al. | 606/213 |

FOREIGN PATENT DOCUMENTS

| EP | 0 542 428 A1 | 5/1993 |
|---|---|---|
| WO | WO 97/07741 | 3/1997 |
| WO | WO 01/89398 A1 | 11/2001 |

* cited by examiner

Primary Examiner—Gary Jackson
(74) Attorney, Agent, or Firm—Oliff & Berridge, PLC

(57) ABSTRACT

A sealing device for a puncture in a blood vessel, device being slidingly receivable over a guide tube and comprising a tubular, resilient sealing member formed with a sealing portion spontaneously sealable upon deployment of the device into an activated state, an engaging portion for bearing against an external surface of the blood vessel and a plurality of anchors fitted at their fore end with fasteners for engaging a corresponding internal surface of the blood vessel and at a rear end with a manipulating bit. The anchors being displaceable between a constricted position in which they blend with the tubular sealing member, and an operative position in which the fasteners are laterally expanded and engage the internal surface of the blood vessel.

37 Claims, 16 Drawing Sheets

DEVICE AND METHOD FOR SEALING A PUNCTURE IN A BLOOD VESSEL

FIELD OF INVENTION

The present invention is generally in the field of homeostatic devices and in particular it is directed to a sealing device for sealing a puncture (incision) in a blood vessel of a patient during or after a medical procedure. The invention is also concerned with a deploying member and a method for deploying the sealing device.

BACKGROUND OF THE INVENTION

During several surgical procedures carried out, for example in treatment of vascular diseases, it is common practice to invade a blood vessel and introduce a treating or diagnostic device, e.g. balloons or various types of stents to operate on walls of the arteries, plaque removing devices, observation and flow diagnostic instruments, etc.

During such procedures, a blood vessel is punctured so as to allow introduction of the instrument through the artery and then maneuver it to the required site of operation. This is carried out in practice by introducing a guide tube often referred to as an "introducer sheath", through which the instrument can then be easily maneuvered to the site of interest.

A problem occurs once the procedure is complete and the guide tube has then to be removed, when the percutaneous puncture bleeds. Bleeding may result in hematoma or in severe cases to malfunction of critical organs and even death. Such bleeding is stopped, by a most common method, by simply applying pressure on to the puncture site by a medically trained person for a sufficiently long period of time until homeostasis takes place to spontaneously seal the puncture and stop the bleeding.

In cases of puncturing the femoral arteries, the required time may be as long as about 45 minutes or more and in some cases re-bleeding occurs if the patient is not in rest.

A variety of methods and devices have been suggested for replacing the traditional method disclosed above, some of which involve introducing chemical compounds which act as homeostasis catalysts or as adhering agents, whilst others aim at introducing various forms of plugging members into the puncture. The following is a list of prior art patents disclosing devices and methods for sealing punctured blood vessels: U.S. Pat. Nos. 4,705,040 4,890,612, 4,929,246, 5,108,420, 5,342,393, 5,350,399, 5,391,183, 5,613,974, 5,810,884, 5,861,003, 5,957,952, 5,984,950, 6,007,563 and WO 98/31287.

It is an object of the present invention to provide a novel and inventive device for sealing a puncture or incision formed in a blood vessel or in other body organs as well as an associated deploying member for deploying the sealing member into a sealing position. A further object of the invention is to provide a method utilizing the sealing member and the associated deploying assembly.

SUMMARY OF THE INVENTION

The present invention calls for a sealing device and an associated deploying assembly, as well as a method for sealing a puncture or an incision formed in a body organ, typically but not limited, in a blood vessel.

By one important feature the present invention, the sealing device is introduced into the puncture over a guide tube (sheath) used for carrying out a medical procedure e.g. angioplasty, in which a probe is introduced into a blood vessel through the guide tube. The sealing member of the present invention is received within a deploying member used for displacing the sealing member into the puncture site and then deploying it into its operative-sealing position, in which it is anchored within the puncture and seals the puncture-incision. The sealing device is fitted with anchoring means to ensure suitable anchorage within the puncture and is useful for a variety of guide tubes on the one hand and for a variety of wall thicknesses of the blood vessel at the puncture site, on the other hand.

In accordance with the present invention there is provided a sealing device for sealing a puncture in a blood vessel, the device being slidingly receivable over a guide tube and comprising a tubular, resilient sealing member formed with a sealing portion spontaneously sealable upon deployment of the device into an activated state, an engaging portion for bearing against an external surface of the blood vessel and a plurality of anchors fitted at their fore end with fasteners for engaging a corresponding internal surface of the blood vessel and at a rear end with a manipulating bit; said anchors being displaceable between a constricted position in which they blend with the tubular sealing member, and an operative position in which the fasteners are laterally expanded and engage the internal surface of the blood vessel.

The present invention also suggests a unique application of a sealing device fitted with means for grabbing tissue of a blood vessel (or any other organ being sealed) surrounding the puncture (i.e. lip or edges of the puncture) and applying force in direction so as to adjoin edges of the puncture, thus reducing the section area of the puncture and speeding the sealing process.

In accordance with a first embodiment of that application, the fasteners are fitted with spikes facing rearwards for engaging tissue of the blood vessel, wherein at the deployed state the anchors are biased radially inwardly, for constricting the size of the puncture in the blood vessel.

According to a second embodiment of that application, there are provided several spears axially displaceable with respect to the resilient sealing member, said spears having a fore end fitted for grabbingly engaging the external tissue surface of the blood vessel at locations peripheral to the puncture. At least said fore end being displaceable radially inwardly so as to decrease the imaginary delimited circle defined by the spears.

The radial inward force applied to the anchor disclosed in the above said first embodiment and to the spears disclosed in the present second embodiment is delivered by the formation of the resilient sealing member which deforms in a manner in which it constricts its diameter adjacent its fore end.

In accordance with another embodiment of the invention, the engaging portion of the sealing member is truncated such that when it is engaged with the blood vessel, the sealing member bears at an inclination over the blood vessel. Accordingly, the fasteners are axially graded, giving rise to an imaginary path extending between edges thereof, said path conforming with the truncated edge of the sealing member.

The sealing device of the present invention is deployable into its operative position by a deploying assembly comprising a tubular housing, a tubular controller received within the housing and a tubular pusher member received within the controller, coaxially received within one another; said pusher adapted for manipulating the sealing member into its activated position.

By manipulating the controller and pusher of the deploying assembly, the sealing member is displaced into the puncture site. The pushing member is fitted with activating surfaces which are fitted with gliding surfaces inclined so as to engage with the manipulating bits at their constricted position and where rotation of the pusher member entails sliding displacement of the manipulating bits about said activating surfaces thereby deploying the anchors into their operative position.

According to one particular embodiment the pusher member also activates the tissue grabbing means into engagement with tissue of the blood vessel surrounding the puncture.

The present invention call also for a method for sealing a puncture in a blood vessel, the method comprising the following steps:
(a) Obtaining a sealing assembly comprising a sealing member fitted within an associated deploying assembly, with a sleeve extending through the sealing assembly, said sleeve defining a through-going path;
(b) Introducing a medical guide tube through the path;
(c) Removing the sleeve;
(d) Carrying out a medical procedure trough the guide tube:
(e) Slidingly displacing the sealing assembly over the guide tube until a fore end of the deploying assembly engages the blood vessel;
(f) Expelling the sealing assembly from the deploying assembly and introducing anchor fastener members of the sealing assembly into the blood vessel through the puncture;
(g) Deploying anchor fastener members into an operative position in which they are laterally expanded and engage the internal surface of the blood vessel;
(h) Disengaging the sealing assembly from the deploying assembly and withdrawing the guide tube, allowing a resilient sealing member formed in the sealing member to spontaneously seal.

According to a particular embodiment at step (d) the guide tube is inserted into the blood vessel at an angle corresponding with a truncation angle of an engaging portion formed at the sealing member, for bearing against an external surface of the blood vessel.

Furthermore, at least step (e) is radio-monitored, whereby at least a fore end of the housing is made of or fitted with a radio-opaque material.

According to a modification of the invention, after the device has been deployed into the puncture site, tissue grabbing means are engaged with the tissue surrounding the puncture and upon applying thereto an inwardly directed radial force, the puncture size is decreased. The tissue grabbing means are either internal spikes e.g. formed on the fasteners and adapted for engaging al internal wall surface of the blood vessel, or spear-like members for engaging external wall surface of the blood vessel.

According to one particular embodiment, where the fasteners are fitted with rearwardly facing spikes, after step (e) axial force is applied to the sealing member in a rearward direction, thereby having the spikes engage tissue of the blood vessel.

BRIEF DESCRIPTION OF THE DRAWINGS

For better understanding the invention and to see how it may be carried out in practice, reference will now be made to the accompanying drawings, illustrating in a non-limiting manner, some embodiments of the present invention, in which.

DETAILED DESCRIPTION OF THE INVENTION

Figure 1:
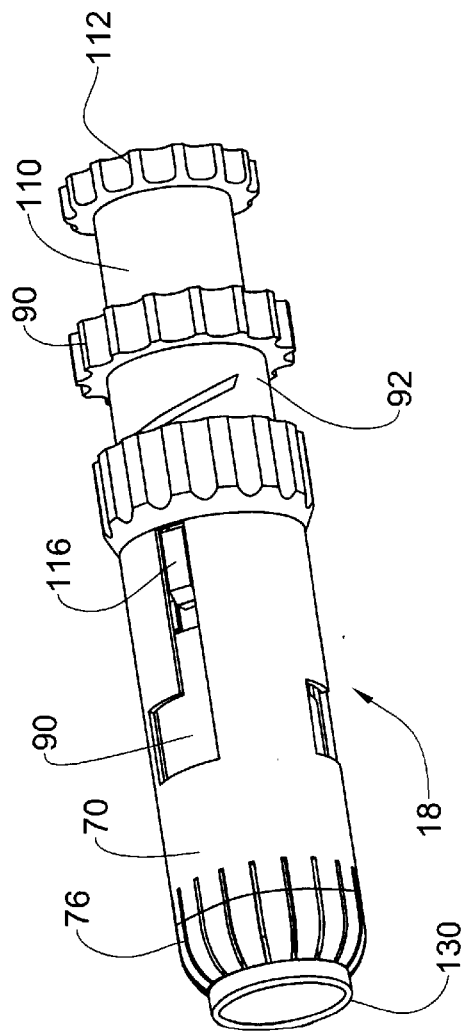
FIG. 1 is an isometric view of a deploying assembly fitted with a sealing member (not seen) in accordance with the present invention, the deploying assembly being at its initial state.
Figure 2:
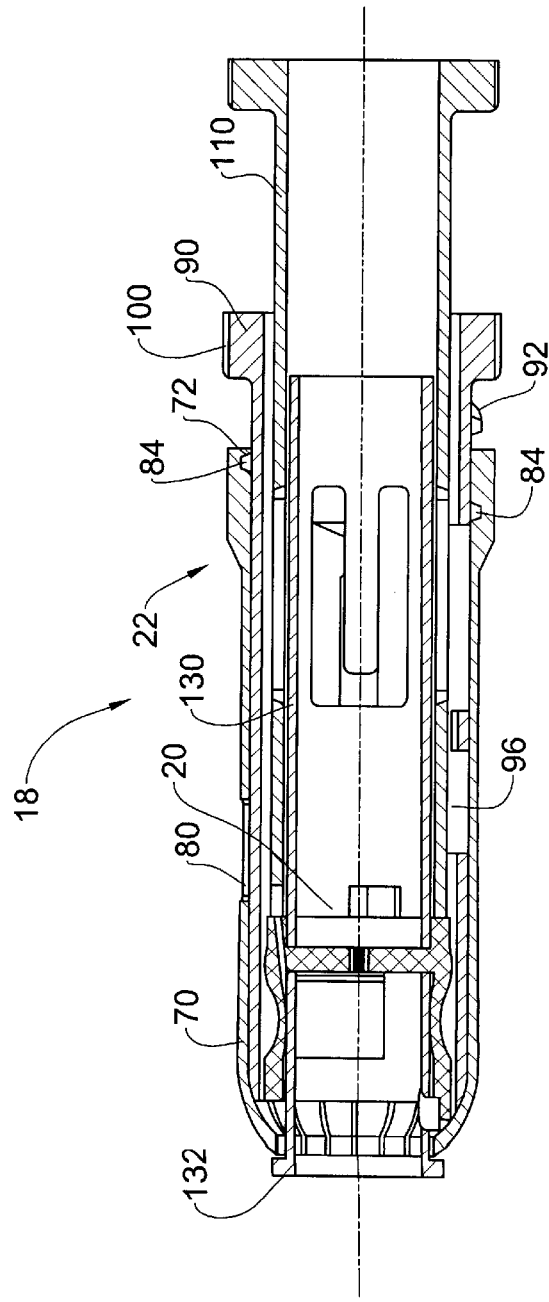
FIG. 2 is a sectional view of the device seen in FIG. 1, visualizing also the sealing member.

Turning first to FIGS. 1 and 2, there is illustrated an assemblage 18 of a sealing device generally designated 20 (FIG. 2) and a deploying assembly generally designated 22.

Figure 3A:
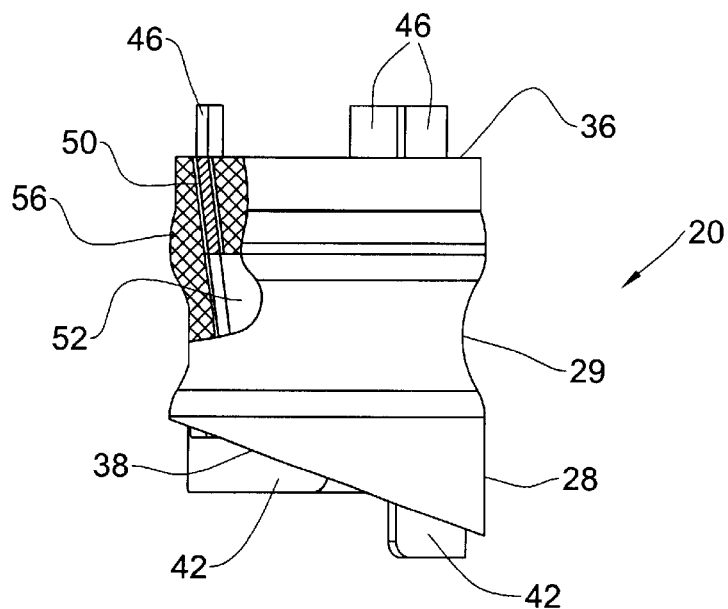
FIG. 3A is a partially sectioned side elevation of the sealing device in accordance with the present invention, in a constricted, non-operative position.
Figure 3B:
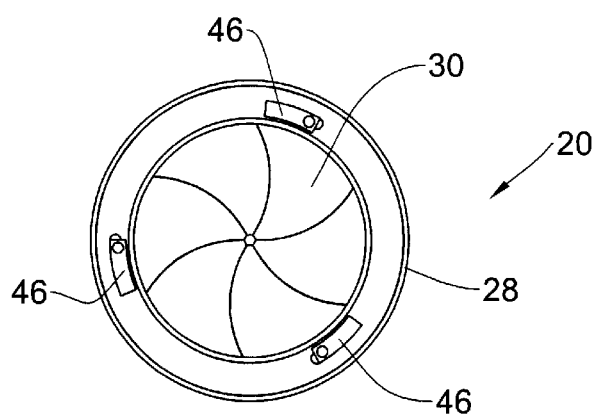
FIG. 3B is a top view of FIG. 3A illustrating a rear end of the sealing device.
Figure 3C:
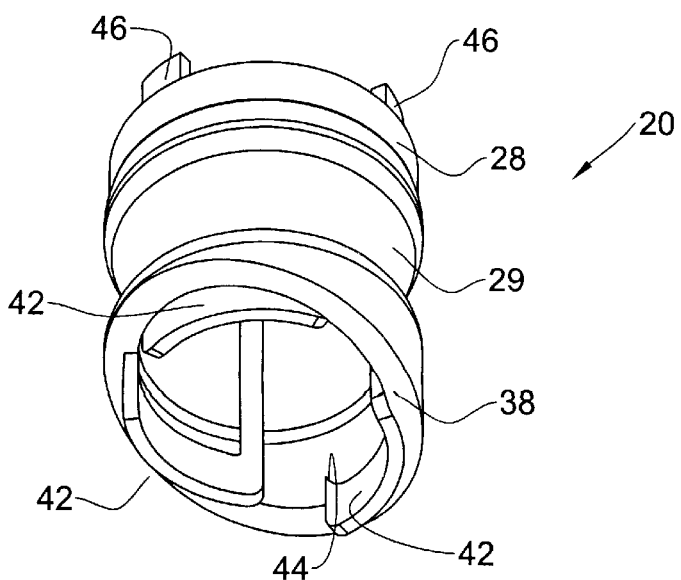
FIG. 3C is a bottom isometric view of the device seen in FIG. 3A.
Figure 4A:
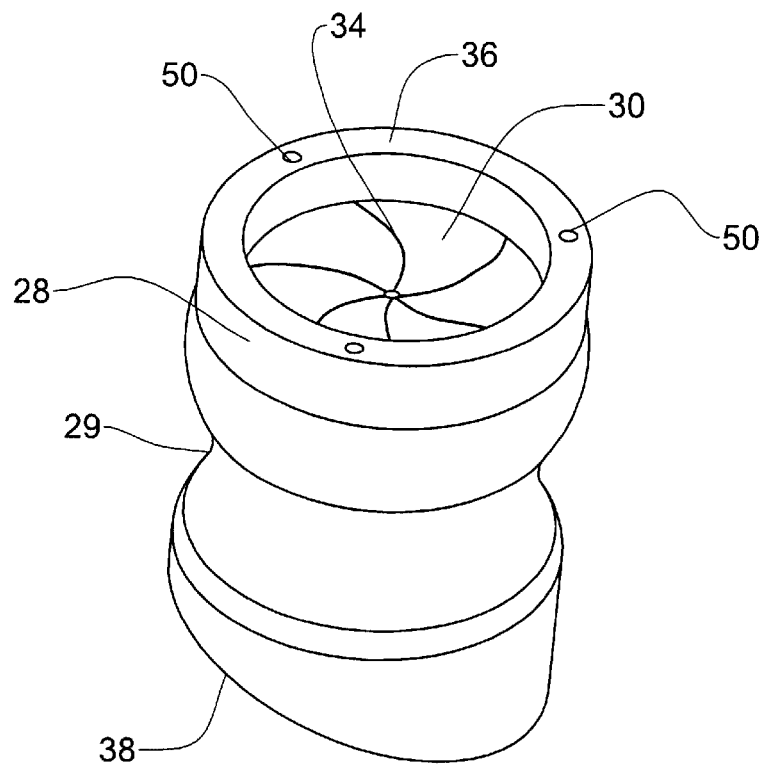
FIG. 4A is a top isometric view of the sealing member, with the anchors removed.
Figure 4B:
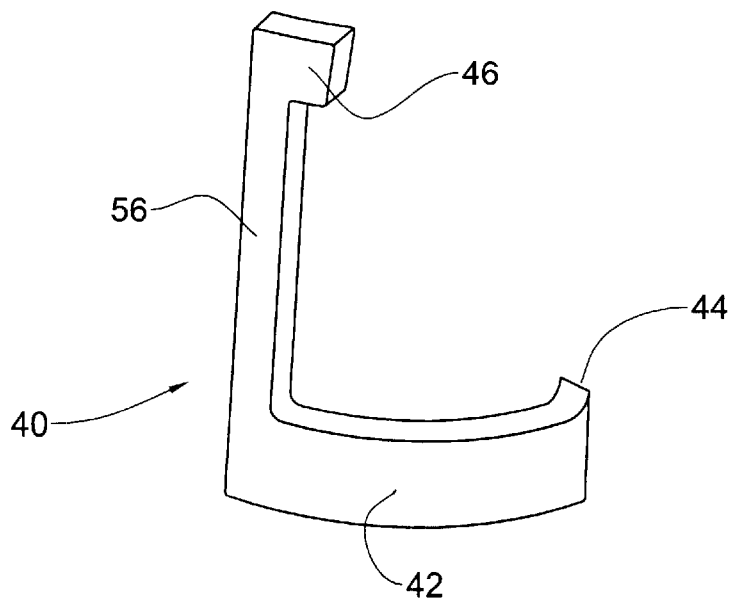
FIG. 4B is an isometric view of an anchor of the sealing device of the in accordance with an embodiment of the present invention.

Further reference will be made to FIGS. 3 and 4 for exemplifying the sealing device 20. The scaling assembly 20 consists of a sealing member 28 having a generally tubular section formed of a resilient material, e.g. silicon rubber. The sealing member 28 is fitted wit a sealing portion 30 which is a diaphragm formed with a plurality of vein-like slots 34. These slots may have different shapes, e.g. plain radial slots, etc. The diaphragm 30 is normally biased to acquire an essentially sealed state. However, any other type of sealing arrangement is possible instead of diaphragm 30.

An intermediate portion 29 of the sealing member 28 is significantly resilient and is axially collapsible upon applying thereto some axial force.

The sealing device 28 has a rear end 36 and a fore end 38 which is a truncated engaging portion adapted for bearing against the external surface of the blood vessel (not shown) and this arrangement is intended for conforming with an insertion angle of typically between about 30° to 45° which the angle at which a medical procedure of inserting an angioplast stent or other procedure is taking place, as known per se.

It is to be appreciated that the sealing member 20 may be formed as a unitary item or may be assembled out of several components. For example, the sealing member may be molded out of several different components, each having different resiliency, etc. Alternatively, the sealing member may be a formed by means of a resilient member received within a housing imparting it regions of varying resiliency as may be required.

The seating member 20 is fitted with three anchors 40 (FIG. 4B) each formed with a fastener 42 for engaging with an internal surface of the blood vessel. Each fastener 42 is formed at its end with a spike 44, the purpose of which will become apparent hereinafter. At a rear end of the anchor 40 there is formed a manipulating bit 46.

Sealing member 28 is formed, in the particular example, with three bores 50 extending at an essentially radially direction (FIG. 3A) from the rear end 36 of the sealing member 28 at a slight inclination inwards. The bores 50 extend only a limited portion of the sealing member 28 and then opens into a common cavity marked 52 of the sealing member 28. A stem portion 56 of anchors 40 is received within bore 50 with the manipulating bits 46 extending above rear end 36 of sealing member 28 and fasteners 42 extending in a graded manner, giving rise to an imaginary path which is essentially parallel to the engaging edge portion 38. This arrangement ensures that when the scaling member 20 is in its activated position engaged within a puncture of a blood vessel, it extends at an oblique angle with essentially similar pressure applied byte three fasteners 42.

Figure 5A:
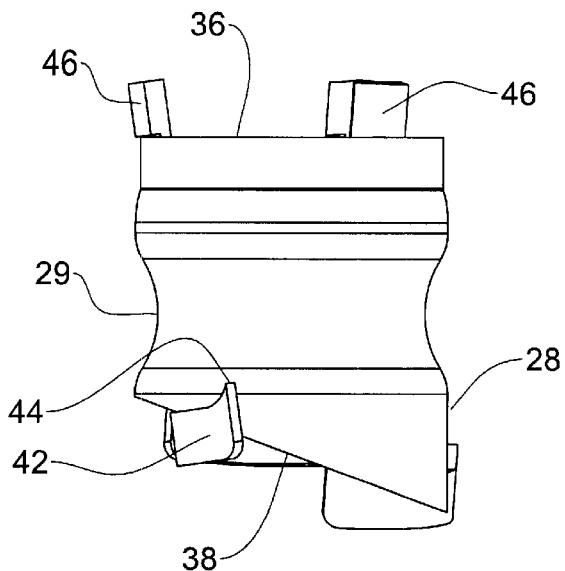
FIGS. 5A, 5B and 5C correspond with FIGS. 3A, 3B and 3C, respectively, in the operative sate of the sealing device.
Figure 5B:
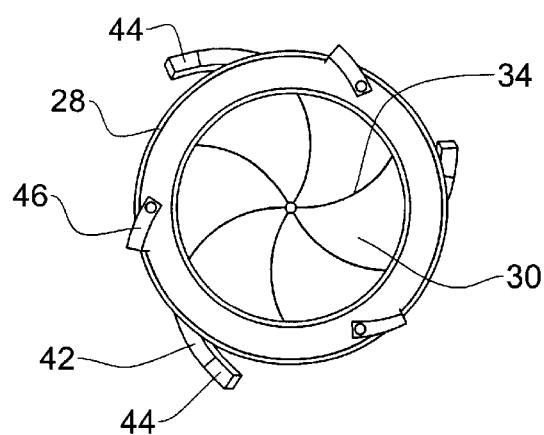
Figure 5C:
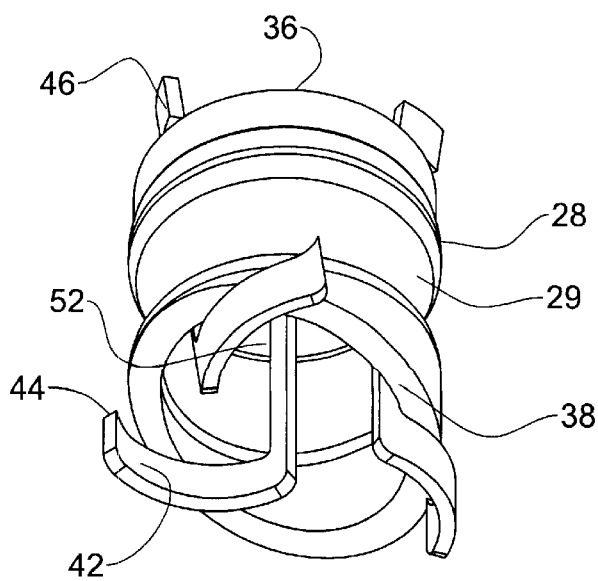

The arrangement is such that a stem portion of each of the anchors 40 is rotatably received within bores 50 between an inoperative position in which the fasteners 42 are constricted and do not extend from the tubular structure of sealing member 28, and an operative position in which the fasteners are laterally expanded for engagement with internal surfaces of the blood vessel, in the position shown in FIGS. 5A to 5C. However, it is to be noted that the stem portion 56 of anchors 40 extend through a common space 52 thin the sealing member 20.

The manner in which the fasteners are shifted into their laterally expanded position will be explained hereinafter with reference to the deploying assembly, As seen in FIG. 2, the sealing device 20 is received within a fore end of the deploying assembly 22.

Figure 6:
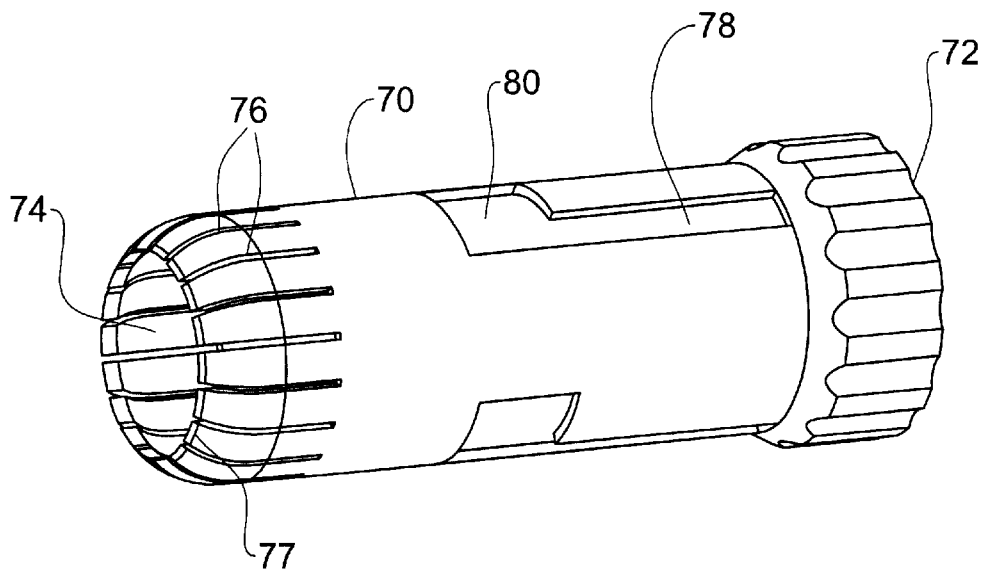
FIG. 6 is an isometric view of the housing of the deploying assembly in accordance wit the present invention.

The deploying assembly comprises a housing 70 (FIG. 6) which is a tubular member formed with an open rear end 72 and an open front end 74. A Am portion of housing 70 narrows towards the font end of the housing and is axially slotted at 76, rendering said front portion resilient whereupon the sealing device 20 may be expelled therethrough as will become apparent hereinafter. Housing 70 is further formed with a plurality of anal slots 78 (Three in the present case) extending axially with a lateral expansion 80 at a fore end of the slot. As can further be seen in FIG. 2, a rear end portion of housing 70 is formed with an internal thread 84 which is adapted for thread engaging with a corresponding thread formed on a connector member 90 (FIG. 7) rotatably engaged within housing 70, whereby rotation of connector 90 yields axial displacement within housing 70.

According to a preferred embodiment of the invention, at least a fore end 77 of the housing 70 is made of or fitted with a radio-opaque portion.

Figure 7:
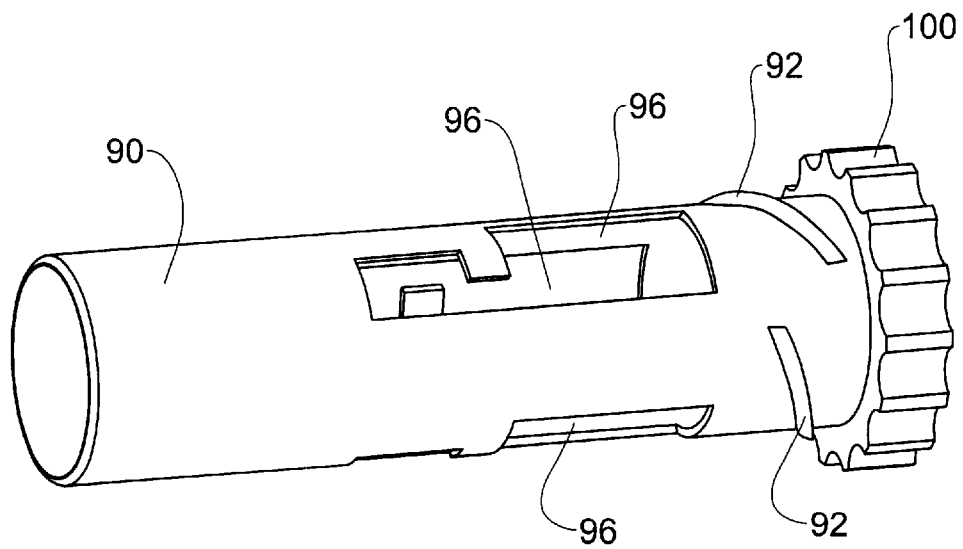
FIG. 7 is an isometric view of a controller of the deploying assembly in accordance with the present invention.

Turning now also to FIG. 7, the connector 90 is illustrated, said connector having a tubular shape snugly receivable within housing 70 and formed with a thread 92 (see also FIGS. 1 and 2) engageable within thread grooves 84. In the particular example the threading is a three-start tread formed with a high pitch. The controller 90 is formed with three openings 96 corresponding with slots 78 and extensions 80 thereof. Controller 90 is fitted at its rear end with a grip portion 100.

Figure 8A:
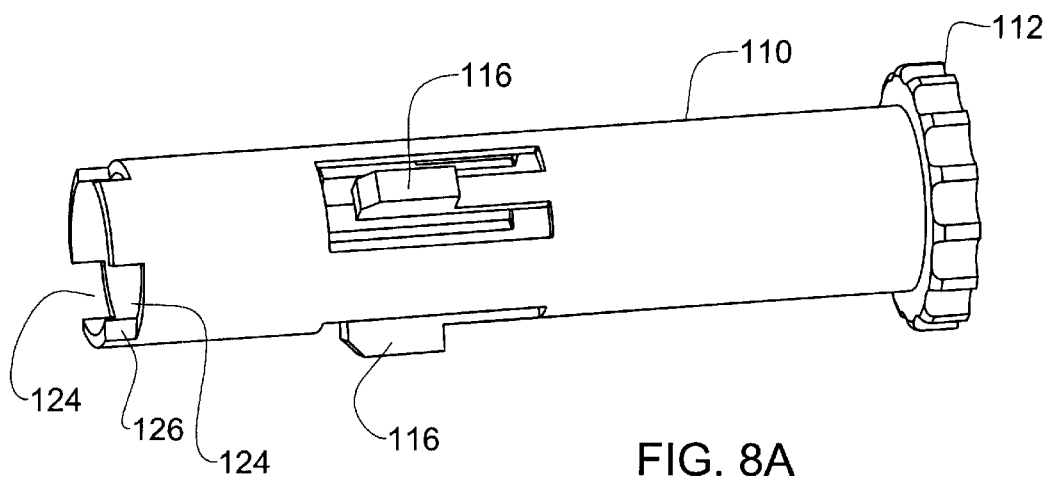
FIG. 8A is an isometric view of a pusher of the deploying assembly in accordance with the present invention.

A pusher member 110 (FIG. 8A) is received within controller 90 and is adapted for axial displacement therewithin. Pusher 110 is formed with a ribbed gripping end 112 and three lateral bulges 116 equi-angularly disposed and adapted for projecting through apertures 96 in controller 90 and recesses 78 in housing 70. The arrangement is such that bulges 116 ensures that the pusher 110 is restricted only to axial displacement with respect to the housing 70 which axial displacement is restricted to the length of recess 78. However, when bulges 116 reach portion 80 of recess 78, the pusher member may be rotated to a limited extent, as represented by arrow 120 in FIG. 10D.

Figure 8B:
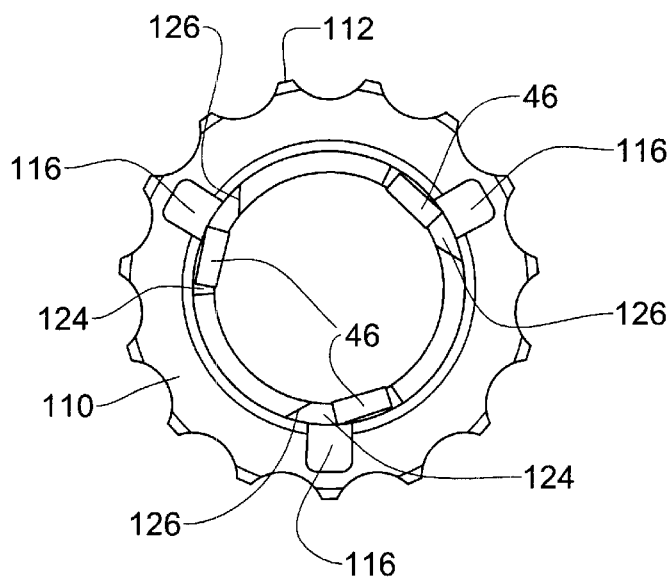
FIG. 8B is a front elevation of the fore end of the pusher member seen in FIG. 8A.

Turning now also to FIG. 8B, a fore end of the pusher 110 is illustrated in which three cut-outs 124 are formed giving rise to a wall 126 cut at a slant serving as a gliding surface. Recesses 124 are sized to accommodate the manipulating tip 46 of anchors 40 whilst surfaces 126 are engageable with said manipulating bits.

Figure 8C:
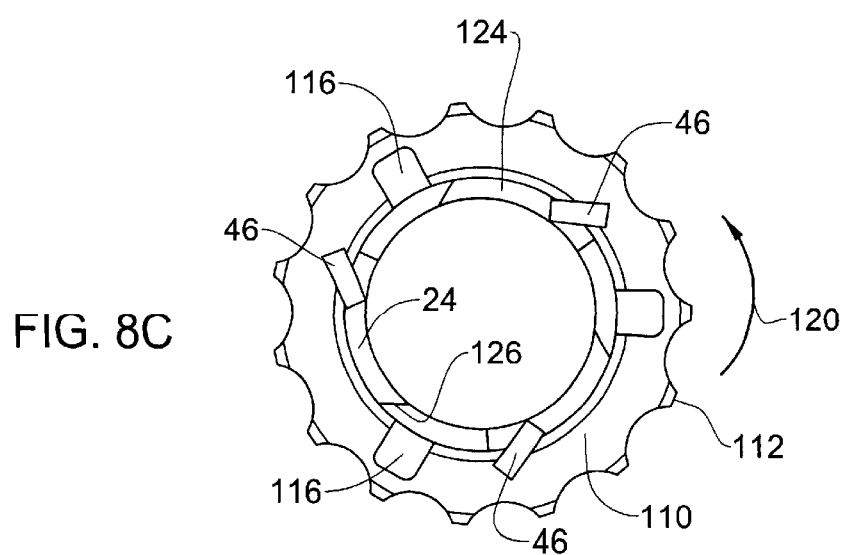
FIG. 8C is a front elevation of the fore end of the pusher member rotated from as seen in FIG. 8B.

At an initial state of the assemblage 18 (FIG. 8B) the recesses 124 of pusher 110 accommodate the manipulating bits 46 in a manner exemplified by one bit only in FIG. 8B illustrated in a solid line. However, upon rotation of the pusher 110 in the direction of arrow 120 (FIG. 8C) thereby imparting axial rotation of anchors 40 within the sealing member 28.

Figure 9:
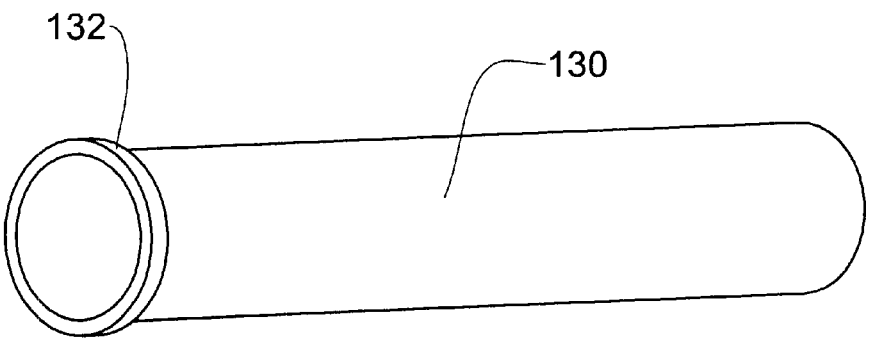
FIG. 9 is an isometric view of a sleeve of the deploying device in accordance with the present invention.

Turning now back to FIGS. 1 and 2, and with further reference to FIG. 9, a tubular sleeve 130 is inserted into the assemblage 18 through a fore end thereof, via opening 74 of the housing. The inner diameter of sleeve 130 is adapted to accommodate a guide tube (also referred to as "sheath") used for carrying out the medical procedure, e.g. during angioplasty.

A fore end of sleeve 130 is fitted with an annular rim 132 for restricting its insertion into the housing and to constitute a gripping member.

In order to avoid mishandling of the device, directing arrows (not shown) are provided on the various components of the deploying assembly, indicating the direction of correct handling. At this stage pusher 110 remains fixed and does not displace with respect to housing 70.

Figure 10A:
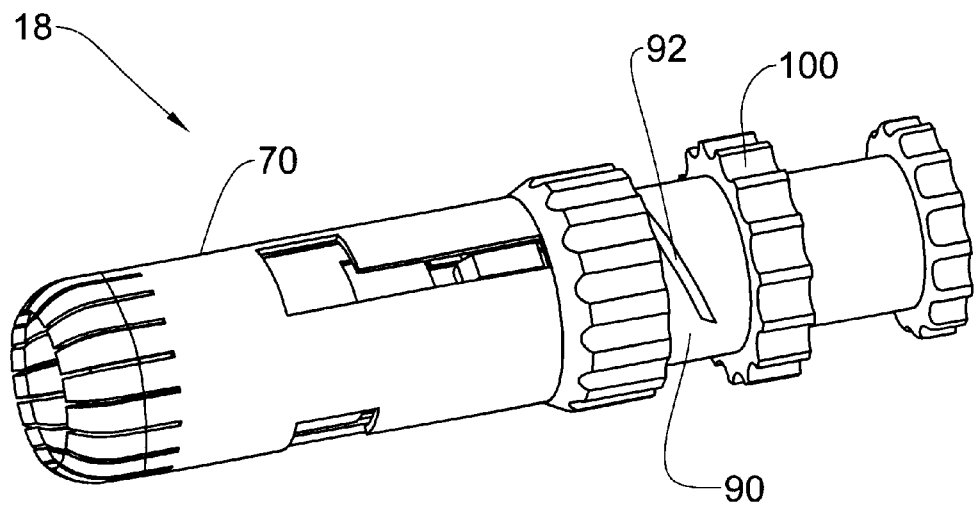
FIGS. 10A–10E represent four consecutive steps of deploying a sealing device in accordance with the present invention, using a deploying assembly of the invention.
Figure 10B:
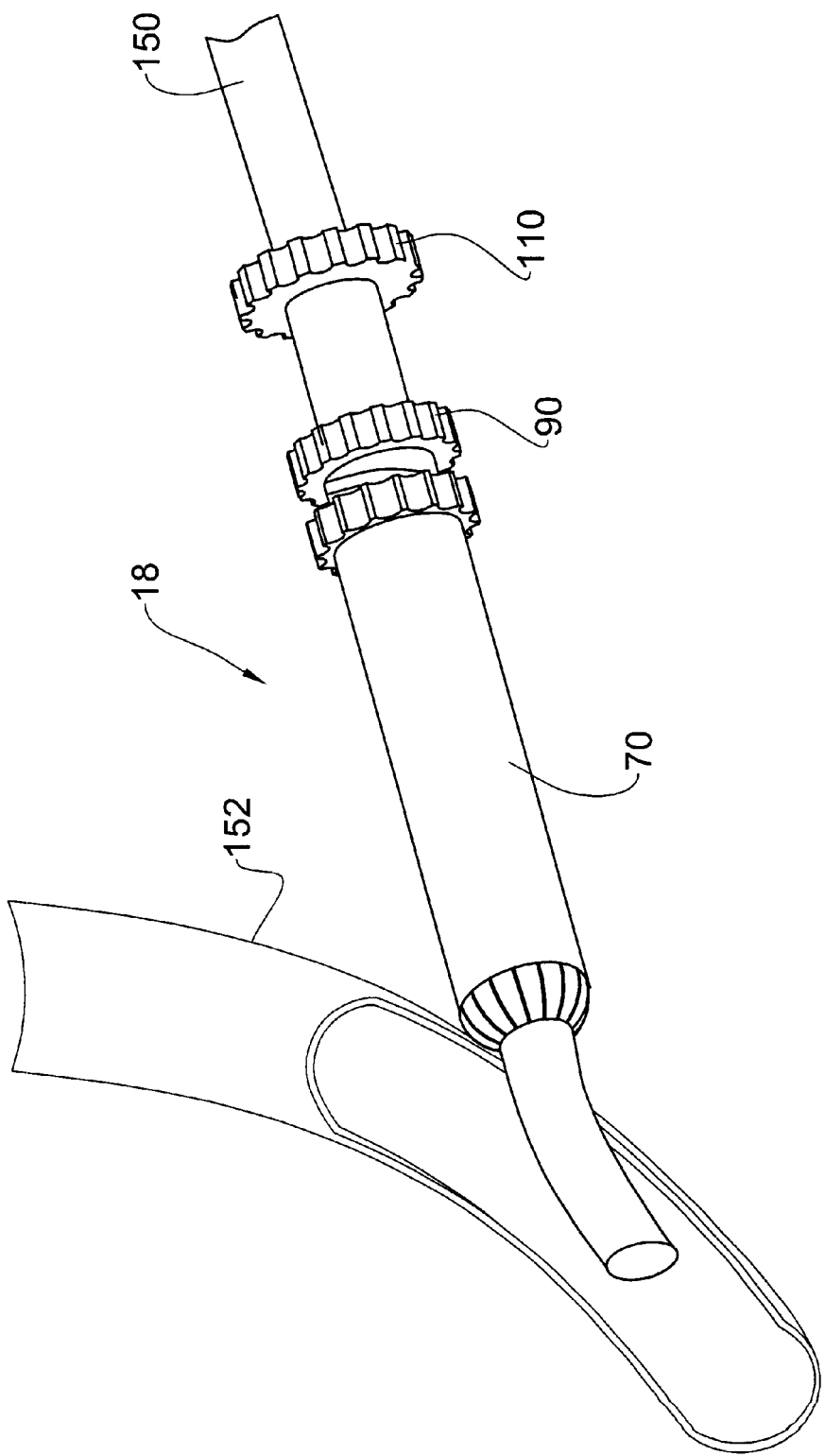

Further attention is now directed also to FIGS. 10A–10E. The assemblage 18 seen in FIG. 2 is mounted on a guide tube (sheath) 150 seen in FIG. 10B and then the sleeve 130 is removed by pulling it at the rim 132. Removing the sleeve 130 causes the sealing device 20 to slidingly engage the guide tube 150. In FIG. 10A, the assemblage 18 is illustrated after having removed the sleeve 130. At this stage, the assemblage 18 is slidingly received over the sheath 150 and the medical procedure, e.g. an angioplasty, takes place by introducing the guide tube 150 into blood vein 152 (FIG. 10B). Typically, the guide tube 150 is introduced into the blood vein at an angle of between about 30 and 45°, depending on the particular medical procedure.

At a next step, after completing the medical procedure, whilst the guide tube 150 is still within blood vessel 152, the physician pushes the sealing assemblage 18 through tissue layers (skin, muscle, etc.) towards the blood vessel 152 by gripping the housing 70 and sliding it along the guide tube 152. This procedure takes place under radiography whereby the radio-opaque portion 77 is visible so that the physician may determine when the fore end of the housing 70 reaches the blood vessel 152.

Figure 10C:
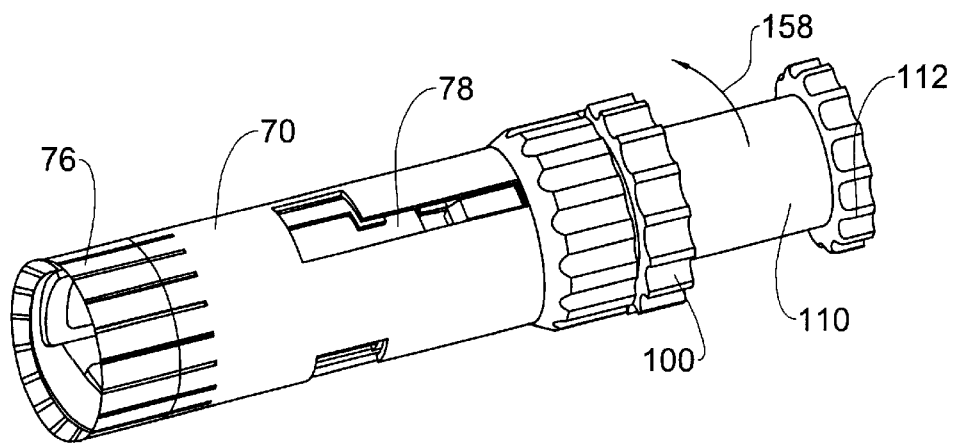

Then, whilst gripping the housing the controller 90 is rotated by gripping it at grip 100 in a direction of arrow 158 in FIG. 10C until fully received within housing 70, thus entailing its axial displacement forwardly within the housing 70. This results in expelling the sealing device forward within the housing 70 giving rise to expanding of the fore end 76 of the housing 70, as seen in FIG. 10C.

Figure 10D:
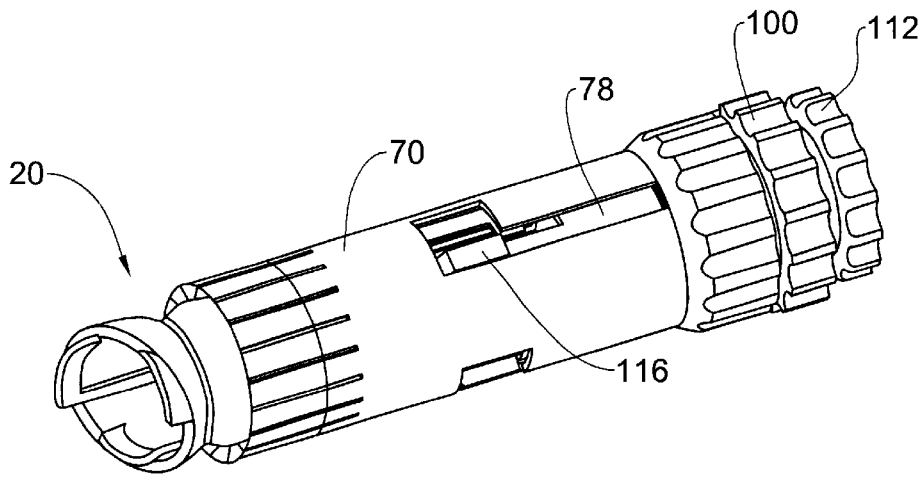

After expanding of the fore end of housing 70 took place, pusher 110 is axially displaced forwardly (FIG. 10D) whereby bulges 116 move within grooves 78 to their forward most position. This maneuver exposes the sealing device 20 as can be seen in FIG. 10D. Upon forward expelling of sealing device 20 the oblique engaging portion 38 of sealing member 28 comes to bear against the external surface of blood vessel 152 whereby further displacement of the device into the blood vessel entails shrinkage of the resilient sealing member 28, in particular at the resilient portion 29, resulting in displacement of the lower portion of the shanks 56 and fasteners 42 of anchors 40 within he blood vessel.

Figure 10E:
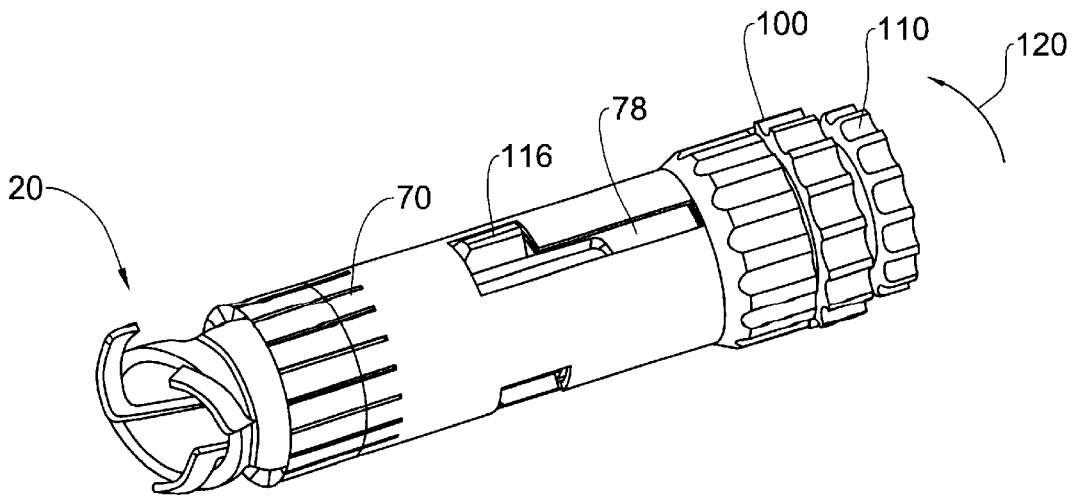
Figure 11A:
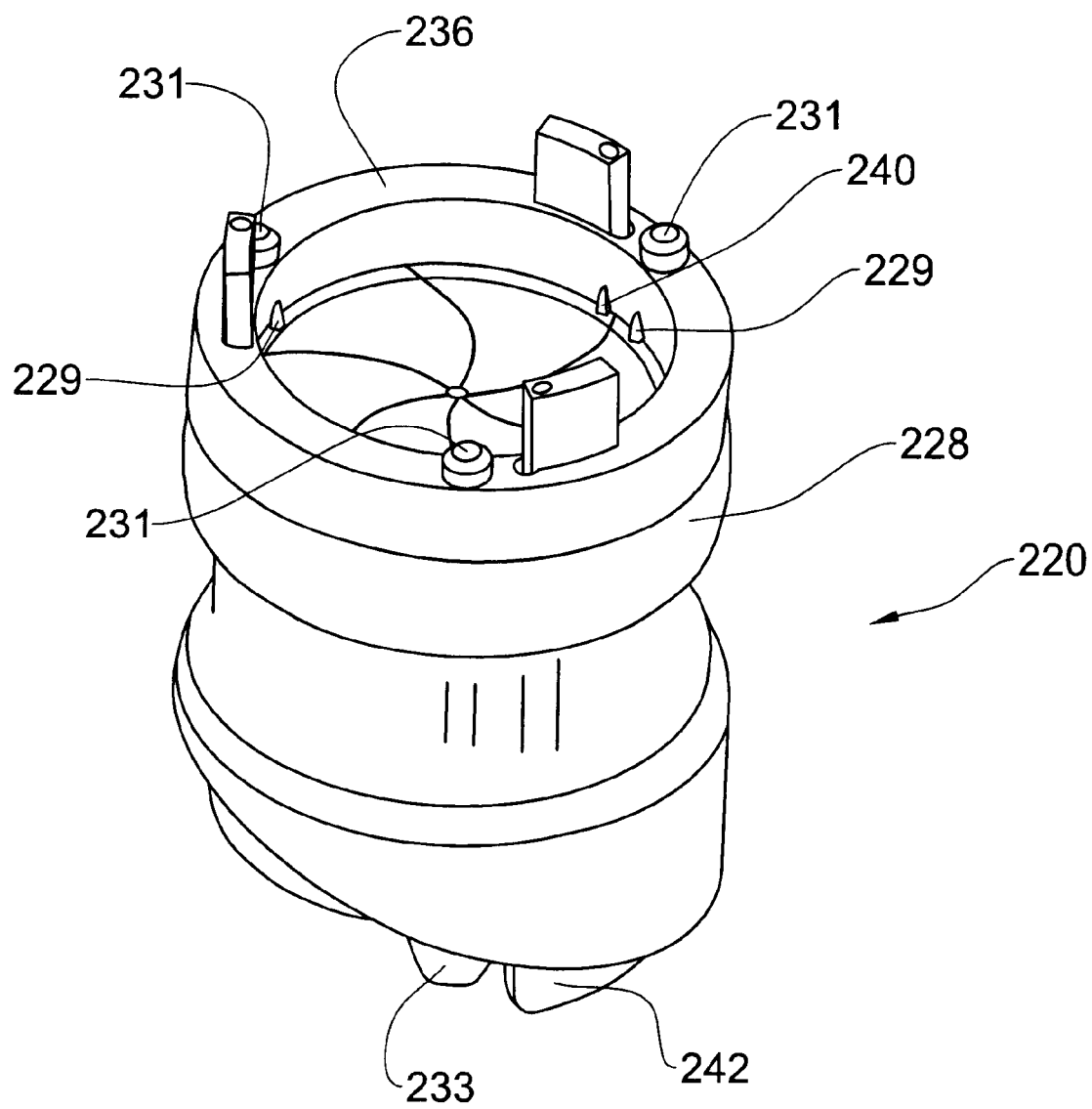
FIG. 11A is a top isometric view of a sealing device in accordance with another embodiment of the invention, the device in its non-operative state.
Figure 11B:
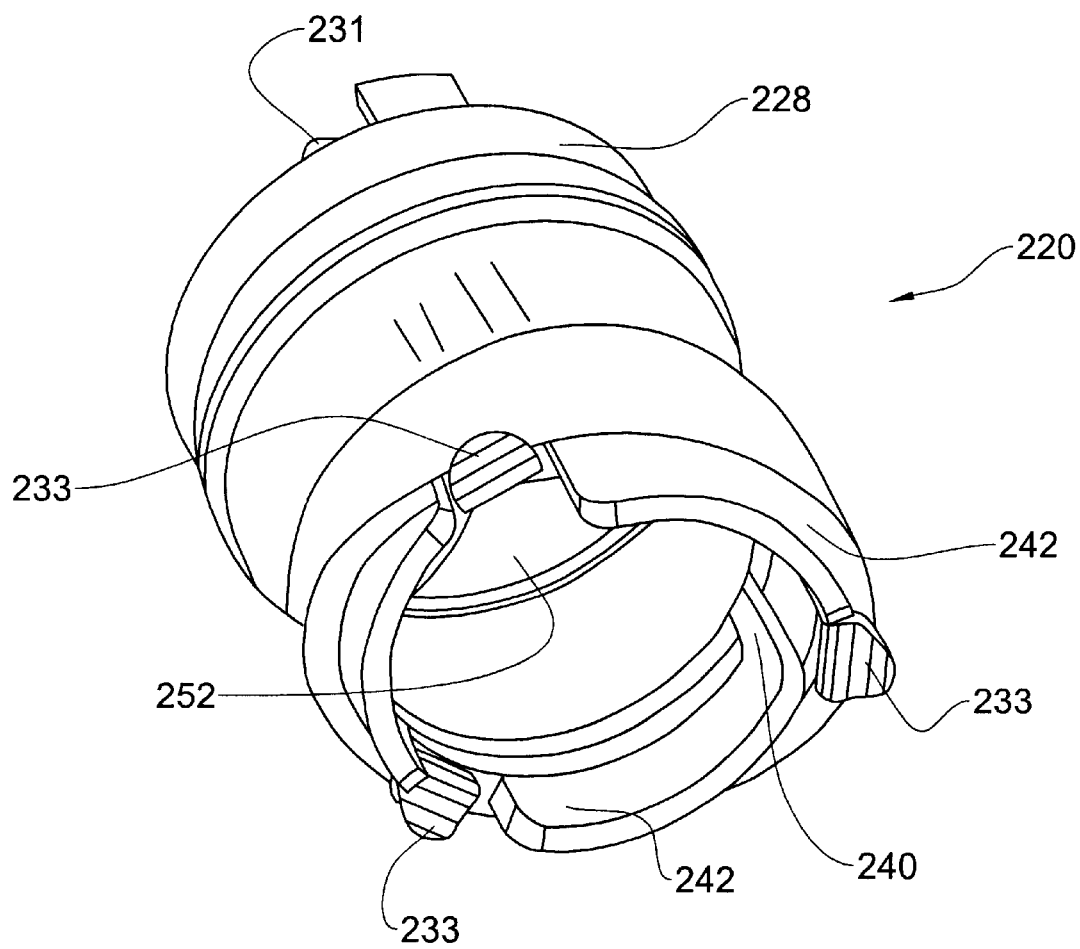
FIG. 11B is a bottom isometric view of the device seen in FIG. 11A.
Figure 11C:
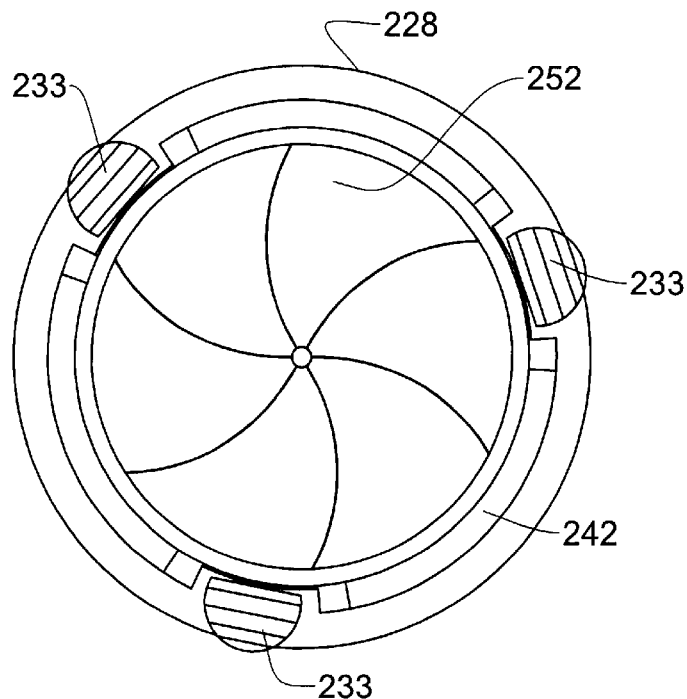
FIG. 11C is a planar view of a fore (bottom) end of the device of FIG. 11A.
Figure 11D:
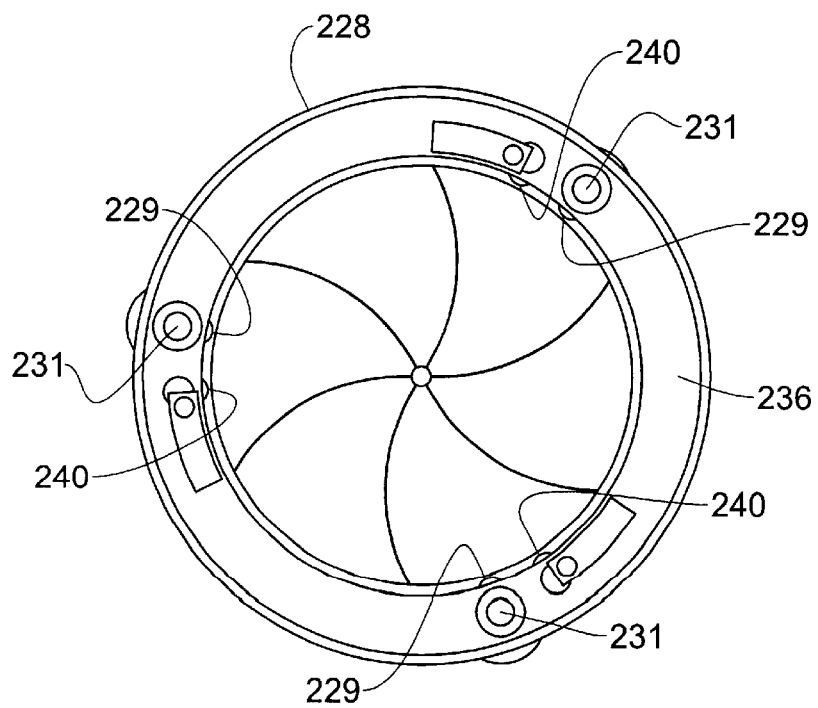
FIG. 11D is a planar view of a rear end of the device of FIG. 11A.
Figure 11E:
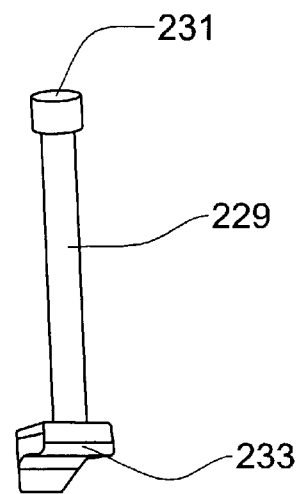
FIG. 11E is an isometric view of a spear received within he scaling device of FIGS. 11A–11D.

In order to anchor the sealing assembly within the puncture of the blood vessel, the pusher 110 is rotated in the direction of arrow 120 in FIG. 10E, allowing bulges 116 to radially displace within the broadened opening 80.

By this rotation, the anchors 40 are axially rotated into he position seen in FIGS. 5A–5C whereby the fasteners are laterally expanded for engaging internal wall surface of the blood vessel at peripheral portions of the puncture formed in the blood vessel.

The physician then applies light force in an outward direction ensuring that spikes 44 engage within the tissue of the blood vessel whereby the device is properly anchored and secured within the puncture of the blood vessel. At a final stage the guide tube 150 is withdrawn allowing the diaphragm 30 to spontaneously close, thereby sealing the sealing device preventing blood flow through. It then remains only to further remove the deploying assembly 22, thereby completing the medical procedure and the puncture in the blood vessel is sealed.

The arrangement is such that the shrinkage of the sealing member 28, in particular at the intermediate portion 29 entails inward radial deflection of the anchors 40, thereby applying some inward radial force urging a constriction of the size of the puncture in the blood vessel for more rapid spontaneous healing thereof.

Figure 12:
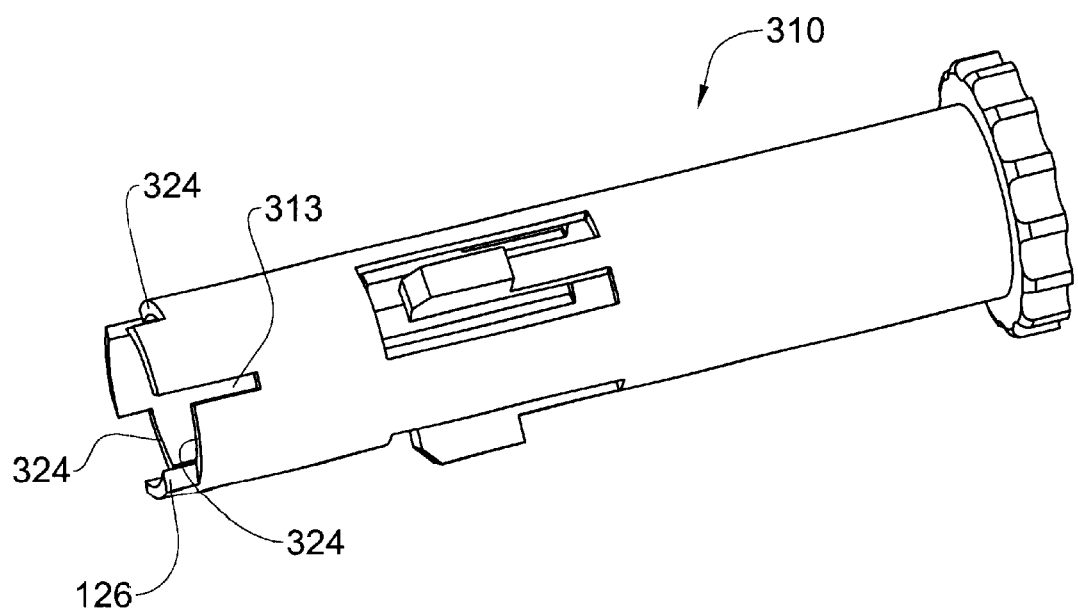
FIG. 12 is an isometric view of a modification of a pusher member used with a sealing device according to the second embodiment illustrated in FIGS. 11A–11E.
Figure 13A:
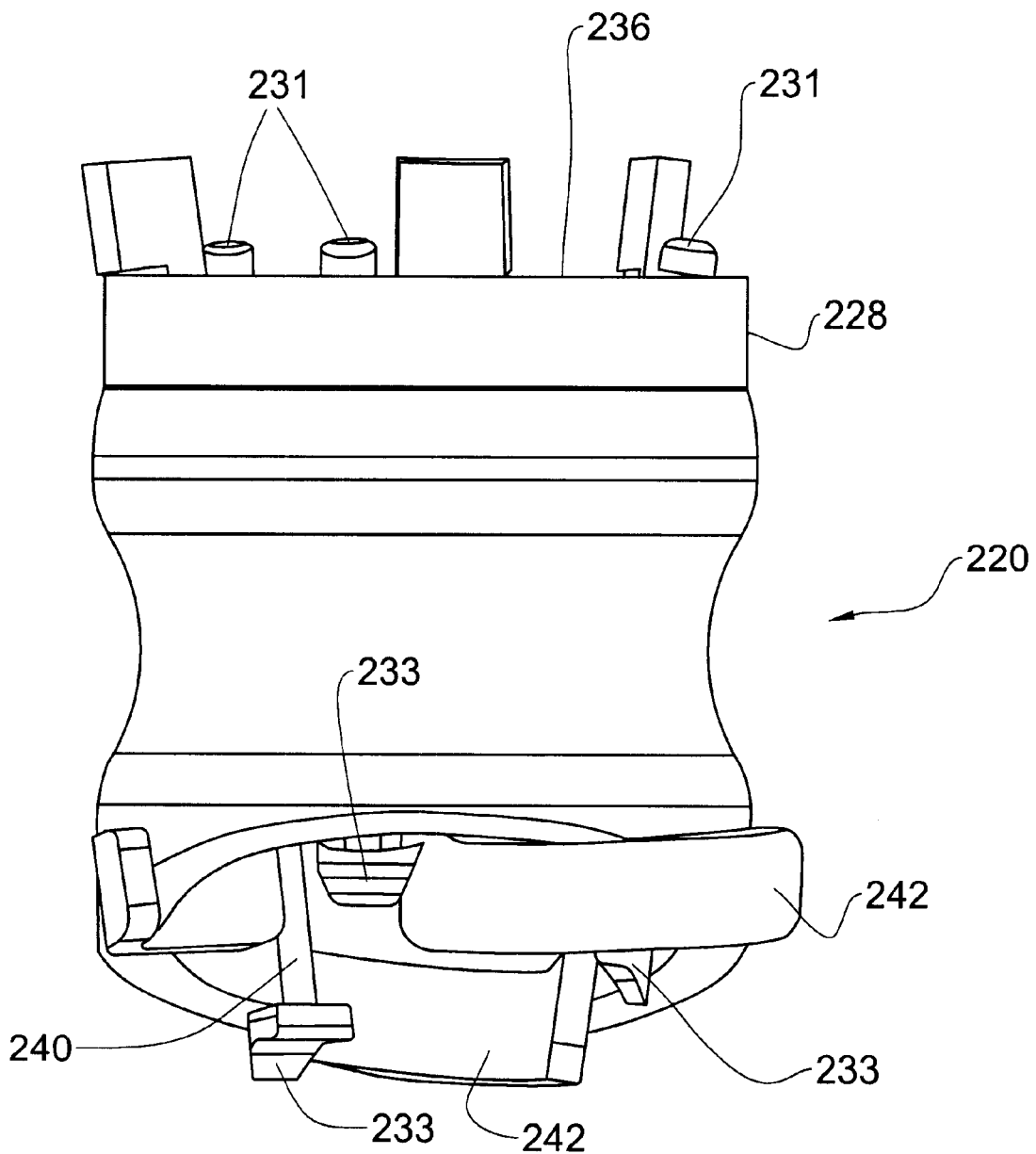
FIG. 13A is a side elevation of the sealing device seen in FIGS. 11A–11D, in the operative state of the device.
Figure 13B:
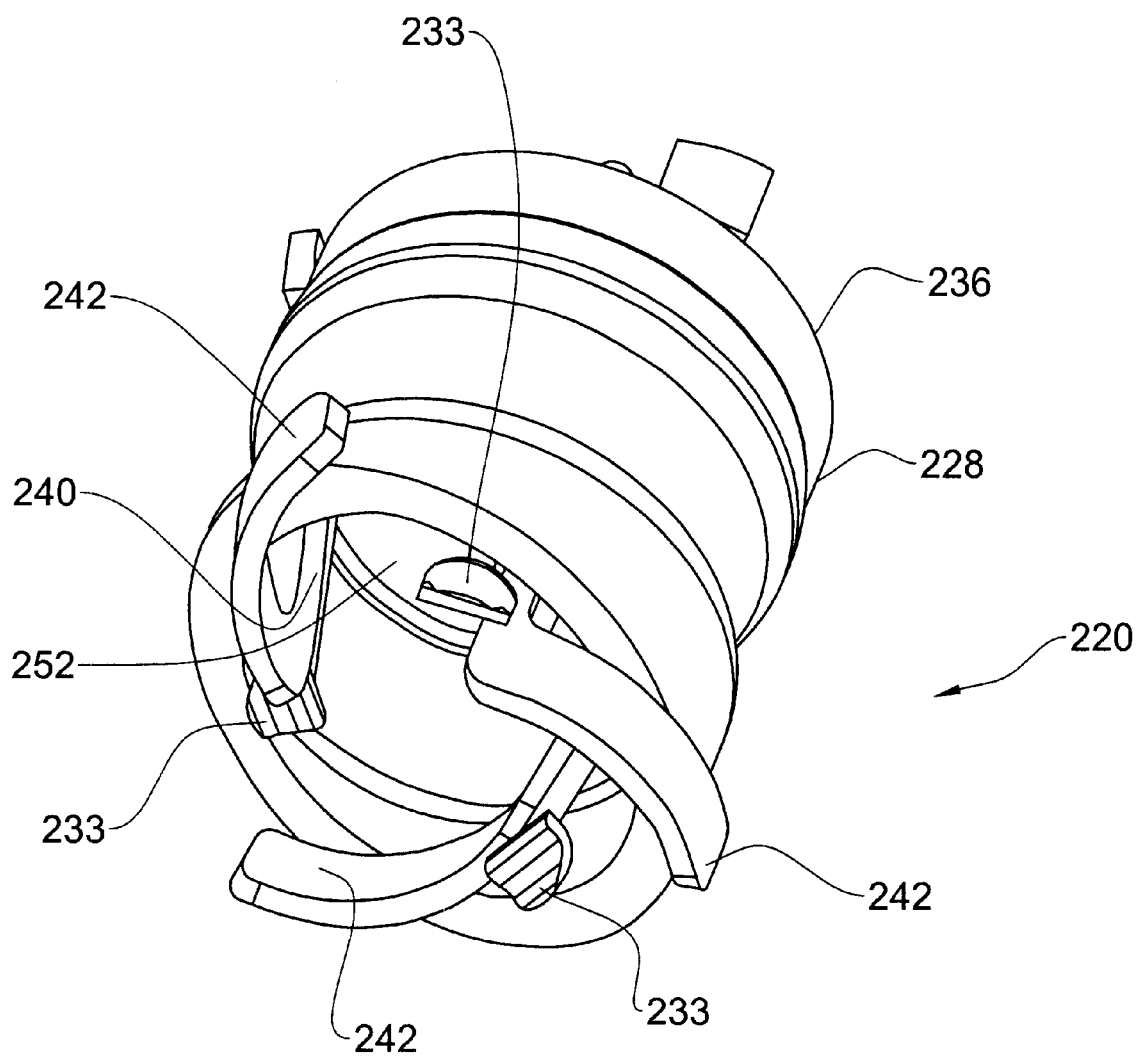
FIGS. 13B–13D correspond with FIGS. 11B–11D, respectively, in the operative state of the device.
Figure 13C:
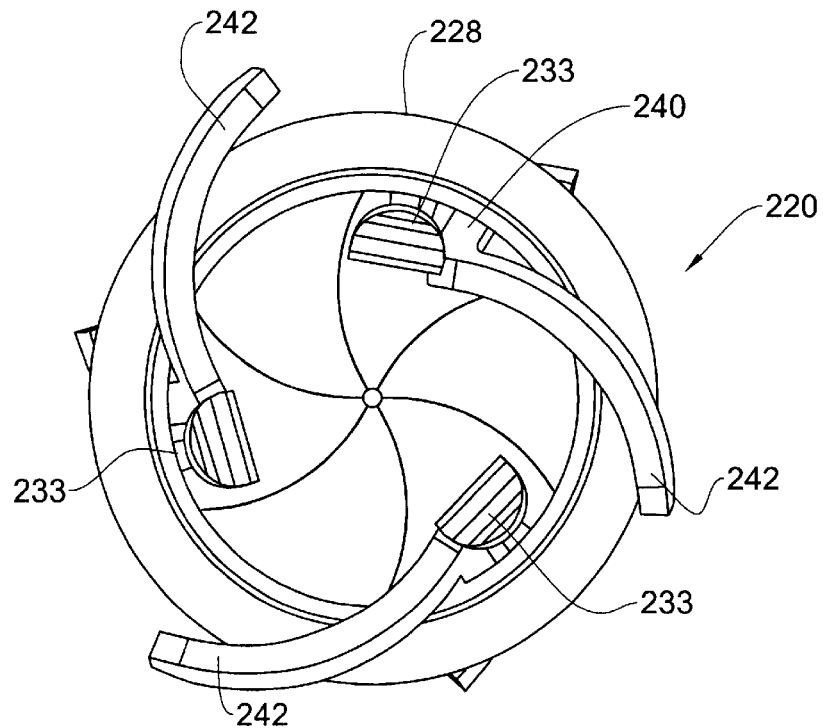
Figure 13D:
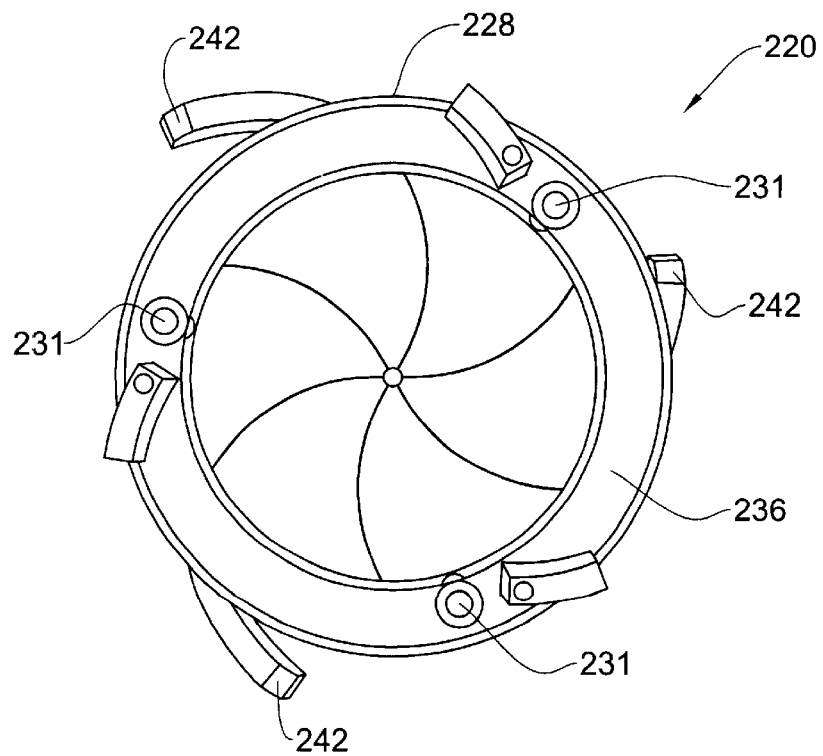

Further attention will now be made to another embodiment of the invention, making reference to FIGS. 11 through 13, illustrating a modified sealing assembly 220 which in FIGS. 11A through 11D is in the non-operative position and in FIGS. 13A through 13D is at an operative position.

The sealing assembly 220 comprises a sealing member 228 which is essentially similar to sealing member 28 in the embodiment of the previous drawings, with the only exception being that it comprises a plurality of bores (tree in the present example), thus, elements which are similar to elements disclosed in connection with the previous embodiment will be designated with corresponding reference numbers shifted by two hundred.

The bores are not visualized in the figures and they axially extend only through a rear portion of sealing member 228. The bores extend from a rear end 36 into a common central cavity 252 (FIGS. 11B, 11C and 13A–13C) of the sealing member 228.

Received within the bores are three spears 229 (FIG. 11E), each having a rear head portion 231 of greater diameter than the bores of the sealing member, thus preventing the spears 229 from unintentional disengagement from the bores. A fore end 233 of each of the spears 229 is pointed such that the edges of the three spears define together an imaginary circular path. A rear stem portion of the spears 229 axially extends through the bore of the sealing member and a fore stem portion of the spear extends in the common space and is radially displaceable inwardly, upon deformation of the sealing member 228.

The sealing device 20 is also fitted with three anchors 240, similar to anchors 40 in the previous embodiment with the only difference residing in that the fasteners 242 lack a rearwardly facing spike 44 and are rather essentially flat though being arranged in a grading pattern, as in the previous embodiment.

The associated pusher member 310 (FIG. 12) for interacting with the sealing device 220 of the present embodiment, is principally similar to pusher 110 of the previous embodiment with an exception that it is formed with three anal recesses 313 each extending from a recess 324. The longitudinal recess accommodates the rear heads 231 of the spears 229 when the pusher member 310 is in its forward position, thus preventing the spears 229 from engaging with tissue.

Operation of the sealing member disclosed hereinabove in connection with the second embodiment is principally similar to that which has been explained and illustrated in connection with the previous embodiment, but with the following exception. After introducing the sealing device 220 into the vicinity of the puncture in the blood vessel and manipulating the deploying member as disclosed with reference to the first embodiment, the fasteners 242 radially expand as in FIGS. 13A–13D (similar to the arrangement of corresponding FIGS. 5A–5C) apart from the spikes. Instead, fore end 232 of spears 229 grabbingly engages into external wall surface of the blood vessel and upon axial deformation of the resilient sealing member 228, the fore ends of the spears are forced in a radially-inward direction, thus adjoining the lips of the puncture at the blood vessel and restricting the puncture's size.

It will be appreciated that the fasteners may also be pointed with spikes, as in the first embodiment, for the same purpose.

Herein the description, reference was made to three spikes and tree spears. It is to be appreciated that this is an example only and any other suitable number of tissue-grabbing means may be used.

Furthermore, a skilled person will appreciate that in fact, the tissue tends to act in a manner to reduce the size of the puncture, i.e. applies force in a direction to spontaneously reduce the sectional area thereof (as the direction of the force is applied on the tissue-grabbing members) and thus assist in the sealing process, Whilst some embodiments have been described and illustrated with reference to some drawings, the artisan will appreciate that may variations are possible which do not depart from the general scope of the invention, mutatis, mutandis.

What is claimed is:

1. A sealing device for a puncture in a blood vessel, the device being slidingly receivable over a guide tube and comprising a tubular, resilient sealing member formed with a sealing portion spontaneously sealable upon deployment of the device into an activated state, an engaging portion for beating against an external surface of the blood vessel and a plurality of anchors fitted at their fore end with fasteners for engaging a corresponding internal she of the blood vessel and at a rear end with a manipulating bit; said anchors being displaceable between a constricted position in which they blend with the tubular sealing member, and an to operative position in which the fasteners are lateral expanded and engage the internal surface of the blood vessel.

2. A sealing device according to claim 1, further comprising a plurality of tissue-grabbing members adapted for engaging with tissue portion surrounding the puncture, and an arrangement for applying to said tissue-grabbing members an inwardly directed radial force.

3. A sealing device according to claim 2, wherein the fasteners are fitted with spikes facing rearwards, for engaging tissue of the blood vessel.

4. A scaling device according to claim 3, wherein at the deployed state the anchors are biased radially inwardly, for constricting the size of the puncture in the blood vessel.

5. A sealing device according to claim 2, wherein the sealing member is fitted with a plurality of spear members for grabbing external wall surface of the blood vessel around the puncture and constricting the size of the puncture by applying thereto force in a radially-inward direction.

6. A sealing device according to claim 5, wherein the spear members have a rear head projecting from a rear end of the sealing member, a rear stem portion axially extending through a bore of the sealing member, a fore stem portion extending through a common cavity of the sealing member and pointed tissue engaging fore ends.

7. A sealing device according to claim 1, wherein the engaging portion of the sealing member is truncated, whereby upon engaging with the blood vessel the sealing member bears at an inclination thereover.

8. A sealing device according to claim 7, wherein the fasteners are axially graded, giving rise to an imaginary path extending between edges thereof, said path conforming with the truncated edge of the sealing member.

9. A sealing device according to claim 1, wherein each anchor comprises a stem portion axially extending along the sealing member, said stem being formed at its rear end with the manipulating bit and at its fore end with the fastener.

10. A sealing device according to claim 9, wherein a first portion of the stem extends through side walls of the sealing member and a second portion of the stem extends within a common cavity of the sealing member.

11. A sealing device according to claim 10, wherein the sealing member is formed with a plurality of bores extending only a portion of the length of the sealing member and rotationally receiving the first portion of each stem.

12. A sealing device according to claim 9, wherein at an operative position of the device the sealing member applies radial force on the stems of the anchors, urging the fasteners radially inwardly for constricting the size of the puncture formed at the blood vessel.

13. A sealing device according to claim 1, wherein the anchors are formed at their aft end with a manipulating bit temporarily engageable by a deploying member for displacing into the operative position.

14. A sealing device according to claim 1, deployable into its operative position by a deploying assembly comprising a tubular housing, a tubular controller received within the housing and a tubular pusher member received within the controller, coaxially received within one another; said pusher adapted for manipulating the sealing member into its activated position.

15. A sealing device according to claim 14, wherein the pusher member has restricted axial displacement with respect to the housing.

16. A sealing device according to claim 15, wherein the pusher member is formed with at least one lateral projection exiting through a corresponding slot formed in the controller and a corresponding slot formed in the housing, thereby restricting the axial displacement of the pusher within the housing.

17. A sealing device according to claim 16, wherein the at least one slot formed in the controller and in the housing are formed at their front ends with a lateral extension allowing for rotation of the pusher member about its longitudinal axis.

18. A sealing device according to claim 14, wherein the pusher member has restricted rotational displacement with respect to the housing.

19. A sealing device according to claim 14, wherein at least a fore end of the housing is radio-opaque material.

20. A sealing device according to claim 14, wherein a fore end of the housing converges to a lesser diameter, said fore end being radially expandable to admit deployment therethrough of the sealing device.

21. A scaling device according to claim 14, wherein a sleeve is fitted into the pusher via the fore end of the housing, said sleeve extending also through the sealing device and retaining it in its constricted position.

22. A sealing device according to claim 14, wherein the controller is axially displaceable within the housing, whereby axially displacement thereof entails intrusion of the sealing member through the fore end of the housing.

23. A sealing device according to claim 14, wherein a fore end of the pusher member is formed with activating surfaces adapted for engagement with the manipulating bits of the anchors and deploying the anchors into the operative position.

24. A sealing device according to claim 23, wherein the activating surfaces are gliding surfaces inclined so as to engage with the manipulating bits at their constricted position and where rotation of the pusher member entails sliding displacement of the manipulating bits about said activating surfaces thereby deploying the anchors into their operative position.

25. A sealing device according to claim 1, wherein the tubular sealing member is biased to axially shrink.

26. A sealing device according to claim 1, wherein the sealing portion is a diaphragm with a normally closed flow path formed by a plurality of slots, intrinsically biased into close the flow path.

27. A sealing device according to claim 1, wherein at least a component of the sealing member is made of a biodegradable or bio-absorbable material.

28. A deploying assembly for deploying a sealing device according to claim 1, comprising a tubular housing, a tubular controller received within the housing and a tubular pusher member received within the controller, coaxially received within one another; said pusher adapted for engagement with the manipulating bits of the sealing device and manipulating the sealing member into its activated position.

29. A method for sealing a puncture in a blood vessel, the method comprising the following steps:
   (a) obtaining a sealing assembly comprising a sealing member fitted within an associated deploying assembly, with a sleeve extending through the sealing assembly, said sleeve defining a through-going path;
   (b) introducing a medical guide tube through the path;
   (c) removing the sleeve;
   (d) carrying out a medical procure through the guide tube:
   (e) slidingly displacing the sealing assembly over the guide tube until a fore end of the deploying assembly engages the blood vessel;
   (f) expelling the sealing assembly from the deploying assembly and introducing anchor fastener members of the sealing assembly into the blood vessel through the puncture;
   (g) deploying anchor faster members into an operative position in which they are laterally expanded and engage the internal surface of the blood vessel;
   (h) disengaging the sealing assembly from the deploying assembly and withdrawing the guide tube, allowing a resilient sealing member formed in the sealing member to spontaneously seal.

30. A method according to claim 29, wherein at step (d) the guide tube is inserted into the blood vessel at an angle corresponding with a truncation angle of an engaging portion formed at the sealing member, for bearing against an external surface of the blood vessel.

31. A method according to claim 29, wherein at least step (e) is radio-monitored, whereby at least a fore end of the housing is radio-opaque material.

32. A method according to claim 29, wherein the anchors are biased radially inwardly, for constricting the size of the puncture in the blood vessel.

33. A method according to claim 29, wherein the fasteners of the fitted with rearwardly facing spikes whereby after step (e) axial force is applied to the sealing member in a rearward direction, thereby having the spikes engage tissue of the blood vessel.

34. A method according to claim 29, wherein the deploying assembly comprises a tubular housing, a tubular controller received within the housing and a tubular pusher member received within the controller, coaxially received within one another; said pusher adapted for manipulating the sealing member into its activated position; wherein step (f) is carried out by the following steps:
   (a) axially displacing the controller within the housing in a forward direction;
   (b) axially displacing the pusher within the controller.

35. A method according to claim 34, wherein the controller and housing are thread-engaged whereby step (a) is carried out by rotating the controller within the housing.

36. A method according to claim 34, wherein a fore end of the pusher member is formed with activating surfaces adapted for engagement with corresponding manipulating bits formed at rear ends of the anchors, whereby deploying the anchors into the operative position of step (g) is carried out by rotating the pusher within the housing.

37. A method according to claim 29, which after step (f) spear members are engaged with an external surface of the blood vessel surrounding to puncture and by applying inwardly directed radial force, the lips of the punctured blood vessel are adjoined, thereby decreasing the size of the puncture.

* * * * *